(12) United States Patent
Geist et al.

(10) Patent No.: US 11,696,750 B2
(45) Date of Patent: Jul. 11, 2023

(54) RETRACTOR DISTRACTOR BLADE SYSTEM

(71) Applicant: Integrity Implants Inc., Palm Beach Gardens, FL (US)

(72) Inventors: Wyatt Drake Geist, Davie, FL (US); Raphael Roybal, Savannah, GA (US); Bradley Sutika, Winston Salem, NC (US)

(73) Assignee: INTEGRITY IMPLANTS INC., Palm Beach Gardens, FL (US)

( * ) Notice: Subject to any disclaimer, the term of this patent is extended or adjusted under 35 U.S.C. 154(b) by 0 days.

(21) Appl. No.: 17/407,065

(22) Filed: Aug. 19, 2021

(65) Prior Publication Data

US 2022/0054120 A1 Feb. 24, 2022

Related U.S. Application Data

(60) Provisional application No. 63/067,462, filed on Aug. 19, 2020.

(51) Int. Cl.
*A61B 17/02* (2006.01)
*A61B 17/86* (2006.01)
*A61B 17/00* (2006.01)

(52) U.S. Cl.
CPC ........ *A61B 17/025* (2013.01); *A61B 17/0206* (2013.01); *A61B 17/86* (2013.01); *A61B 2017/00477* (2013.01); *A61B 2017/0256* (2013.01)

(58) Field of Classification Search
CPC ............. A61B 17/0206; A61B 17/025; A61B 2017/0256
USPC ................................................. 600/201–246
See application file for complete search history.

(56) References Cited

U.S. PATENT DOCUMENTS

| 9,414,828 | B2 * | 8/2016 | Abidin ................ A61B 17/025 |
| 9,795,370 | B2 | 10/2017 | O'Connell et al. |
| 9,962,147 | B2 | 5/2018 | O'Connell et al. |
| 2012/0296171 | A1 | 11/2012 | Lovell et al. |
| 2013/0190575 | A1 | 7/2013 | Mast et al. |
| 2016/0074029 | A1 | 3/2016 | O'Connell et al. |
| 2020/0253593 | A1 * | 8/2020 | Wilson ................ A61B 17/025 |

* cited by examiner

*Primary Examiner* — Eduardo C Robert
*Assistant Examiner* — Christina Negrellirodriguez
(74) *Attorney, Agent, or Firm* — McHale & Slavin, P.A.

(57) ABSTRACT

The invention involves a retraction distraction blade system suitable for use with retractor and distractor tools for the implantation of intervertebral implants into the spine area of an animal, particularly humans. The retractor distractor blade includes structures for attaching the blade to a retractor or distractor tool to provide visual access to a surgical site. The blade is provided with a threaded member connected to a flexible lasso for securement around a portion of a pedicle screw or bone screw. Once the lasso is secured to the pedicle screw, the retractor is prevented from moving out of the surgical site. Operation of the distractor or retractor tool can then be utilized to provide distraction to the spinal vertebrae for implant insertion or spinal alignment. Once the procedure is sufficiently complete, the lasso can be removed from the pedicle screws.

19 Claims, 11 Drawing Sheets

RETRACTOR DISTRACTOR BLADE SYSTEM

RELATED APPLICATIONS

In accordance with 37 C.F.R 1.76, a claim of priority is included in an Application Data Sheet filed concurrently herewith. Accordingly, the present invention claims priority to U.S. Provisional Patent Application No. 63/067,462, entitled "RETRACTOR DISTRACTOR BLADE SYSTEM", filed Aug. 19, 2020. The contents of the above referenced application are incorporated herein by reference in its entirety.

FIELD OF INVENTION

The present invention generally relates to providing a pathway to the internal anatomy of an animal; and more particularly, to a retractor distractor providing an expanded pathway through the tissue and expanded spacing between bones for inserting an implant in the spine of an animal such as a human.

BACKGROUND INFORMATION

A normal human spine is segmented with seven cervical, twelve thoracic and five lumbar segments. The lumbar portion of the spine resides on the sacrum, which is attached to the pelvis. The pelvis is supported by the hips and leg bones. The bony vertebral bodies of the spine are separated by intervertebral discs, which reside sandwiched between the vertebral bodies and operate as joints, allowing known degrees of flexion, extension, lateral bending and axial rotation.

The intervertebral disc primarily serves as a mechanical cushion between adjacent vertebral bodies, and permits controlled motions within vertebral segments of the axial skeleton. The disc is a multi-element system, having three basic components: the nucleus pulposus ("nucleus"), the annulus fibrosus ("annulus") and two vertebral end plates. The end plates are made of thin cartilage overlying a thin layer of hard, cortical bone that attaches to the spongy, richly vascular, cancellous bone of the vertebral body. The plates thereby operate to attach adjacent vertebrae to the disc. In other words, a transitional zone is created by the end plates between the malleable disc and the bony vertebrae. The annulus of the disc forms the disc perimeter, and is a tough, outer fibrous ring that binds adjacent vertebrae together. The fiber layers of the annulus include fifteen to twenty overlapping plies, which are inserted into the superior and inferior vertebral bodies at roughly a 40-degree angle in both directions. This causes bi-directional torsional resistance, as about half of the angulated fibers will tighten when the vertebrae rotate in either direction.

It is common practice to remove a spinal disc in cases of spinal disc deterioration, disease or spinal injury. The discs sometimes become diseased or damaged such that the intervertebral separation is reduced. Such events cause the height of the disc nucleus to decrease, which in turn causes the annulus to buckle in areas where the laminated plies are loosely bonded. As the overlapping laminated plies of the annulus begin to buckle and separate, either circumferential or radial annular tears may occur. Such disruption to the natural intervertebral separation produces pain, which can be alleviated by removal of the disc and maintenance of the natural separation distance. In cases of chronic back pain resulting from a degenerated or herniated disc, removal of the disc becomes medically necessary.

One known technique to address many such spinal conditions is commonly referred to as spinal fixation. Surgical implants are used for fusing together and/or mechanically immobilizing adjacent vertebrae of the spine. Spinal fixation may also be used to improve the position of the adjacent vertebrae relative to one another so as to alter the overall alignment of the spine. Such techniques have been used effectively to treat the above-described conditions and, in most cases, to relieve pain suffered by the patient.

One particular spinal fixation technique includes immobilizing the spine by using orthopedic rods, commonly referred to as spine rods, which run generally parallel to the spine. This is accomplished by exposing the spine posteriorly and fastening bone screws to the pedicles of the appropriate vertebrae. The pedicle screws are generally placed two per vertebra, one at each pedicle on either side of the spinous process, and serve as anchor points for the spine rods. Clamping elements adapted for receiving a spine rod therethrough are then used to join the spine rods to the screws. The clamping elements are commonly mounted to the head of the pedicle screws. The aligning influence of the rods forces the spine to conform to a more desirable shape. In certain instances, the spine rods may be bent to achieve the desired curvature of the spinal column.

Drawbacks to the procedure may include infection, blood loss and nerve damage from accessing the disc space. Thus, what is needed is a device for accessing the disc space. The device should also function to provide distraction of the disc space for insertion of the intervertebral spacer. Still yet, the device should utilize the placement of pedicle screws to provide a suitable anchor for distraction of the bones for insertion of the intervertebral implant.

The retractor distractor blade must be easily and quickly assembled to various known retractors or distractors using minimal hardware and requiring a minimal number of tools. Further, the retractor distractor blade must assemble to the retractor and/or distractor in such a way so as not to detract from the intended use of the cannula.

Thus, the present invention provides a blade system for retractors and/or distractors used for spinal surgery which overcomes the disadvantages of prior art retractor and distractor blades. The retractor distractor blade system of the present invention not only provides for relative ease in the assembly and use, it also permits spinal implant implantation without the need to use secondary tools that block the vision pathway of the surgeon.

SUMMARY OF THE INVENTION

Briefly, the invention involves a retraction distraction blade system suitable for use with retractor and distractor tools for the implantation of intervertebral implants into the spine area of an animal, particularly humans. The retractor distractor blade includes structures for attaching the blade to a retractor or distractor tool to provide visual access to a surgical site. The blade is provided with a threaded member connected to a flexible lasso for securement around a portion of a pedicle screw or bone screw or alternatively the blade may be provided with a flexible clamping member for forcing the pedicle screw against a portion of the blade to provide three point contact between the blade assembly and the pedicle screw. While the preferred embodiment includes the threaded member positioned along the longitudinal axis of the blade, the threaded member may be oriented in any desired orientation suitable for connection to the lasso. This construction allows the threaded member to be rotated from outside of the surgical site. Once the lasso(s) or clamping member is/are used to secure the pedicle screw(s) the retractor is prevented from unwanted moving out of the surgical site. Operation of the distractor or retractor tool can then be utilized to provide distraction to the spinal vertebrae, as the tool is normally operated, for implant insertion or spinal alignment. Once the procedure is sufficiently complete, the lasso or clamping member can be removed from contact with the pedicle screws. In some embodiments, the tulip portion of the pedicle screw may be secured to the pedicle screw after the blade is released from the pedicle screw.

Accordingly, it is an objective of the present invention to provide a retractor distractor blade that provides a clear field of view to the surgical site.

It is a further objective of the present invention to provide a distractor retractor blade constructed for placing an intervertebral implant in the disc area of an animal.

It is yet a further objective of the present invention to provide a retractor distractor blade that provides both the function of retraction of tissue to provide access to the surgical site, as well as providing bone distraction for insertion of intervertebral implants and spinal alignment.

It is another objective of the present invention to provide a retractor distractor blade that secures to pedicle screws to provide distraction of the bones.

Other objectives and advantages of this invention will become apparent from the following description taken in conjunction with the accompanying drawings wherein are set forth, by way of illustration and example, certain embodiments of this invention. The drawings constitute a part of this specification, include exemplary embodiments of the present invention, and illustrate various objects and features thereof.

BRIEF DESCRIPTION OF THE FIGURES

FIG. 2B is a partial top view illustrating the unimpeded view provided by the present retractor distractor blade when providing distraction to the spinal joint;

DETAILED DESCRIPTION OF THE PREFERRED EMBODIMENTS

Figure 1:
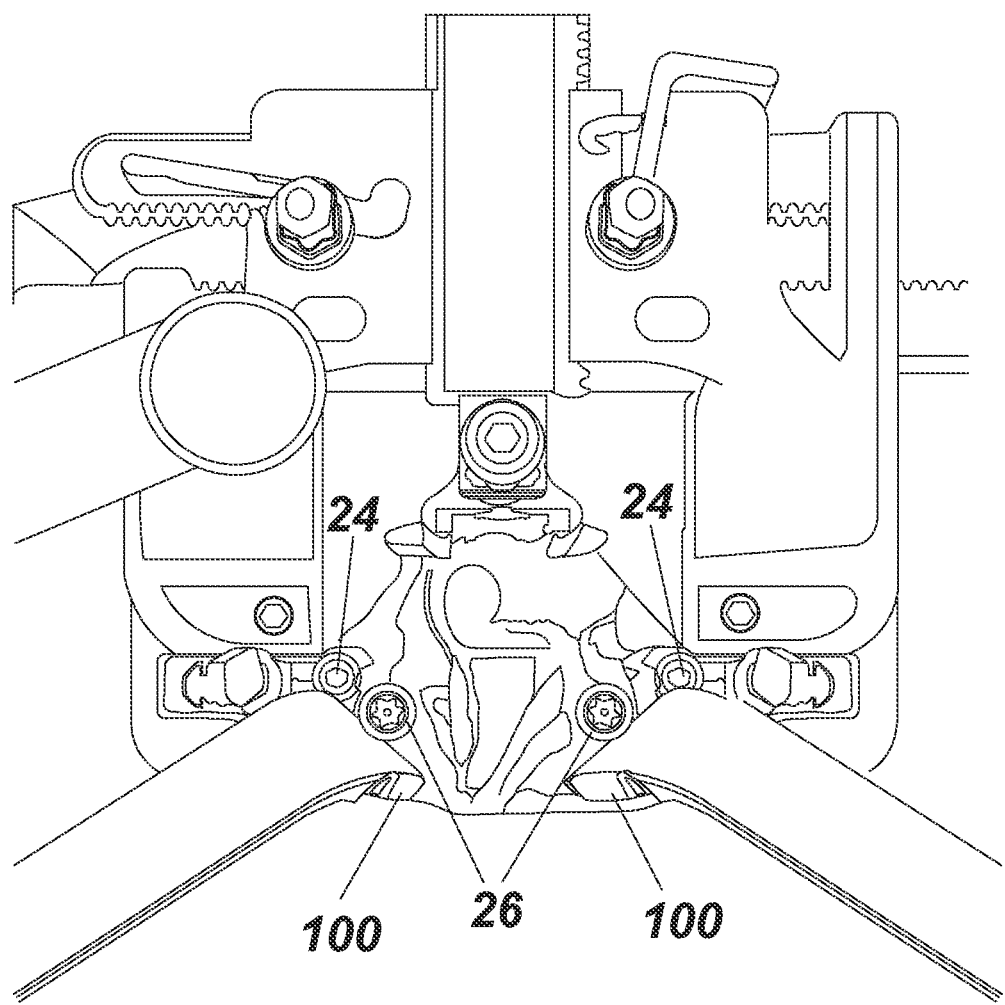
FIG. 1 is a top perspective view of one embodiment of the present invention, illustrating the retraction distraction blade in cooperation with one type of retractor tool.
Figure 2A:
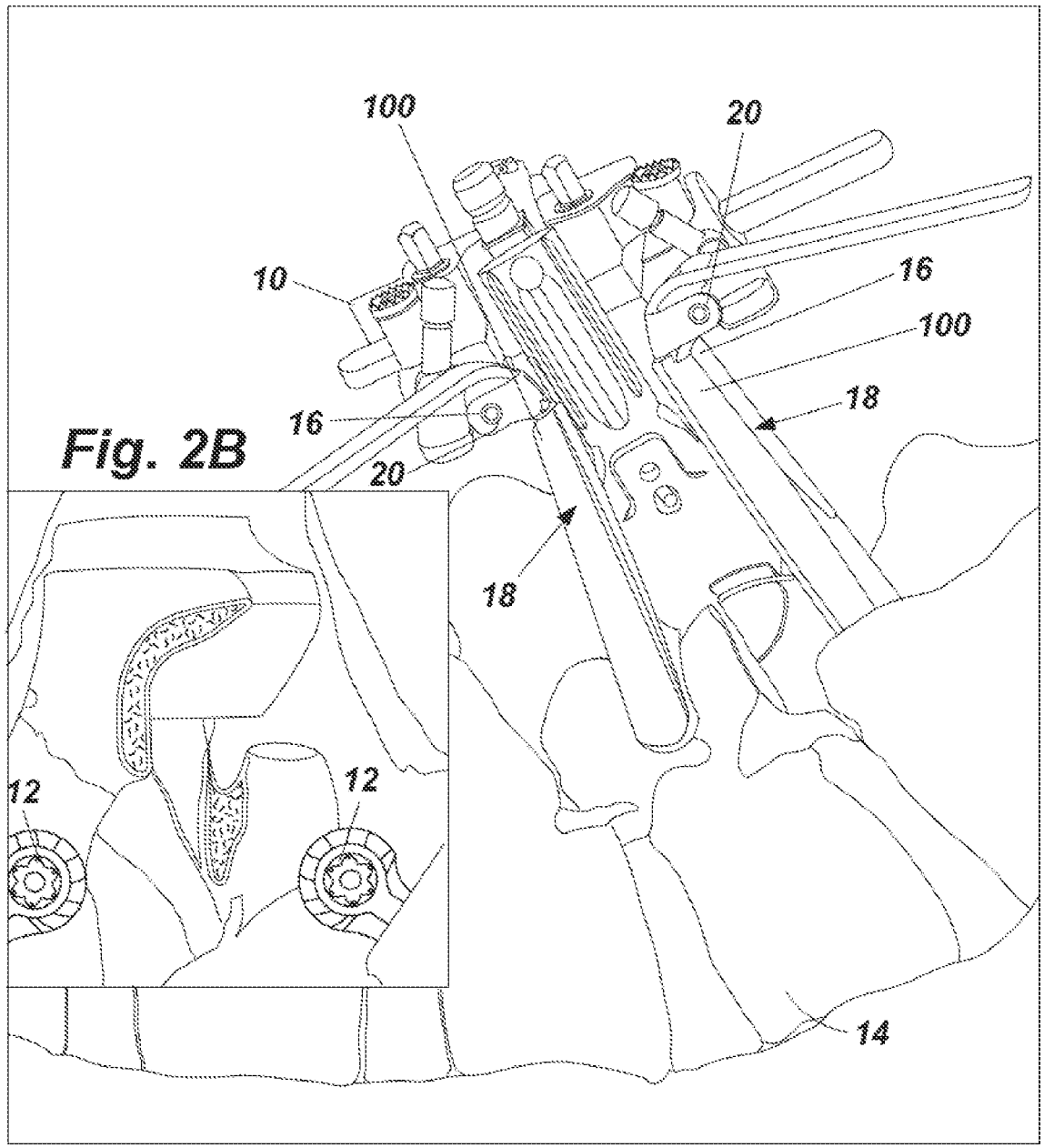
FIG. 2A is a side view of the embodiment shown in FIG. 1, illustrating the retraction tool and retractor distractor blades cooperating with pedicle screws.
Figure 3:
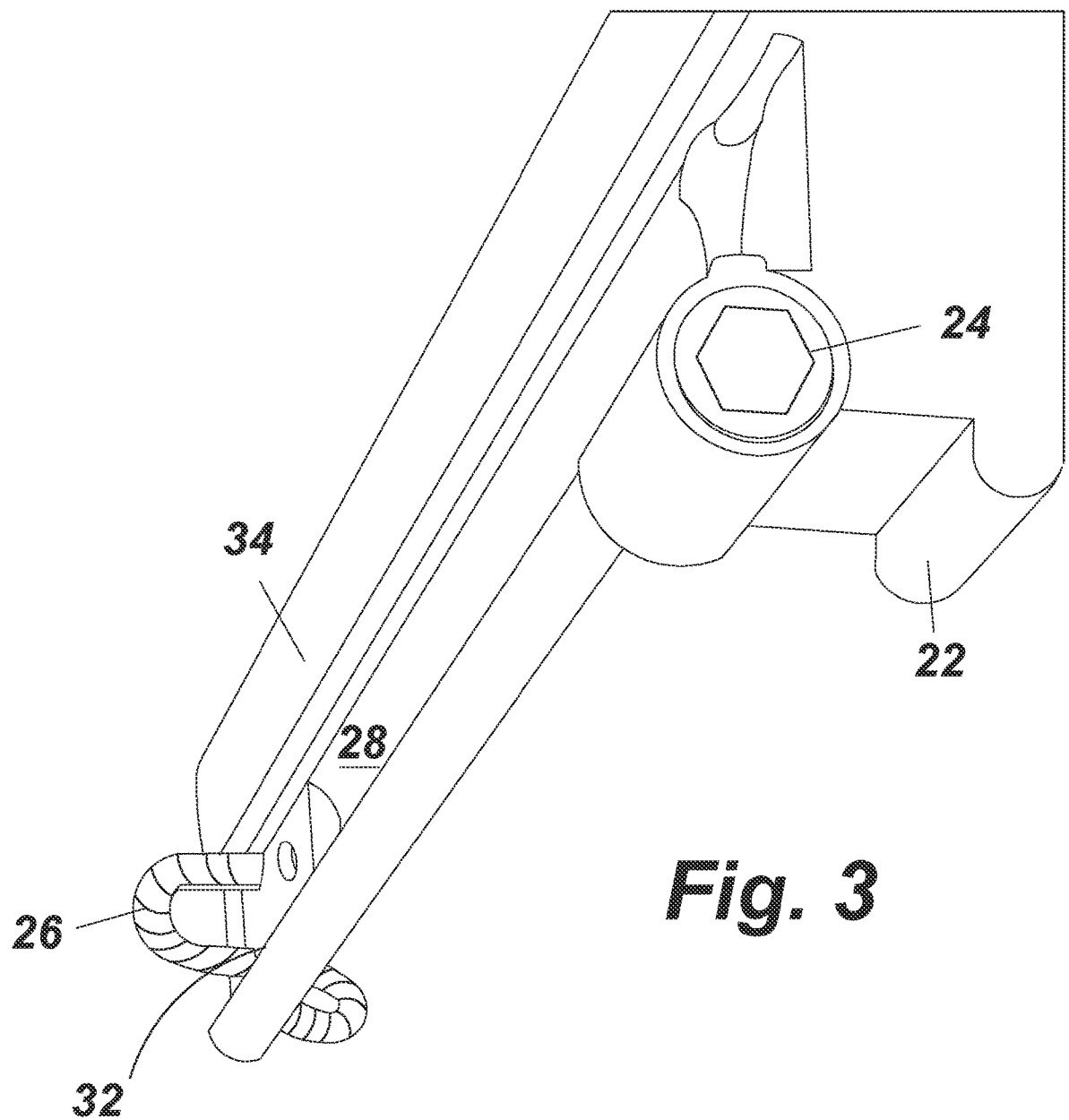
FIG. 3 is a top front right perspective view illustrating one embodiment of the retractor distractor blade.
Figure 4:
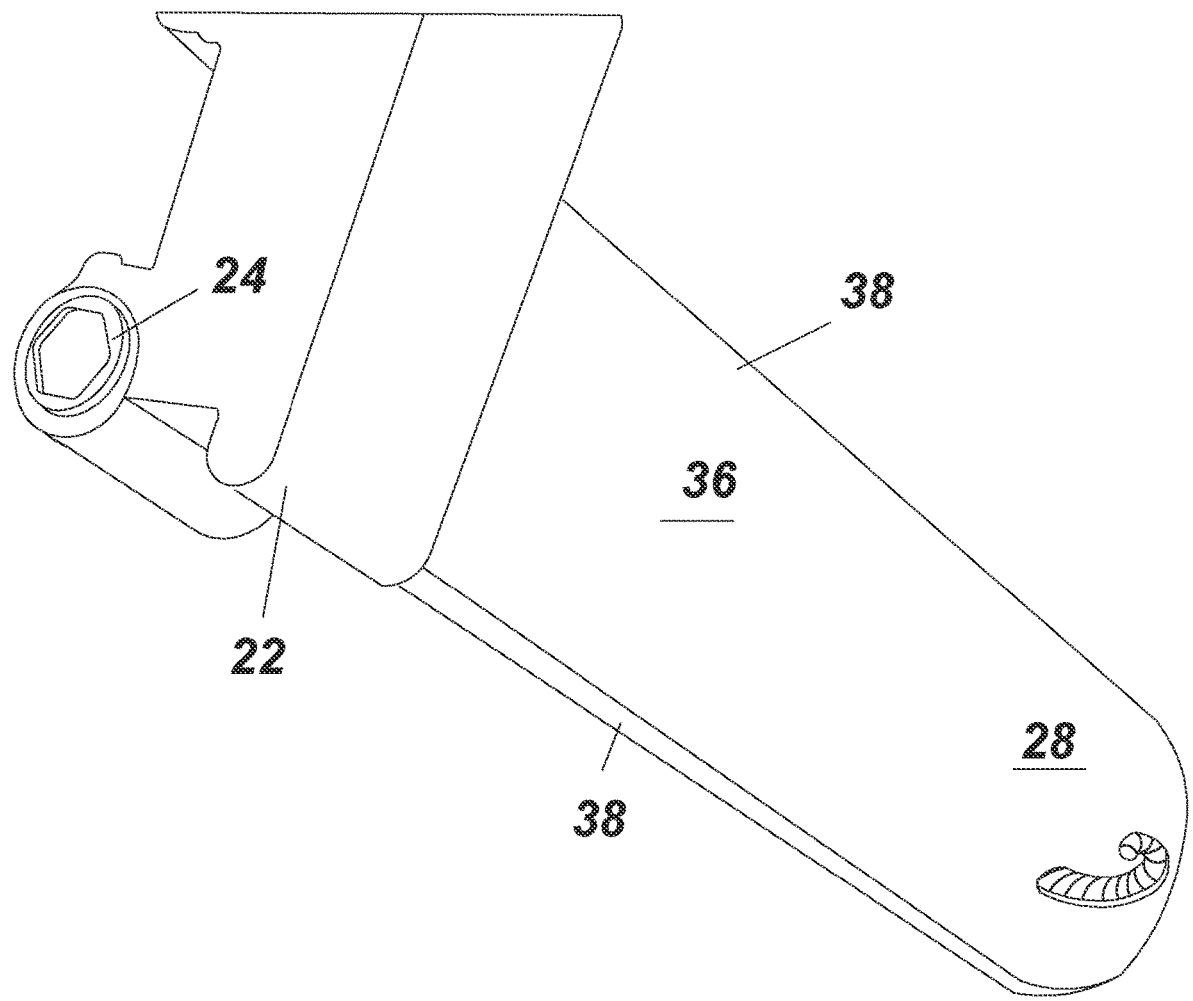
FIG. 4 is a top right rear perspective view of the retractor distractor blade.
Figure 5:
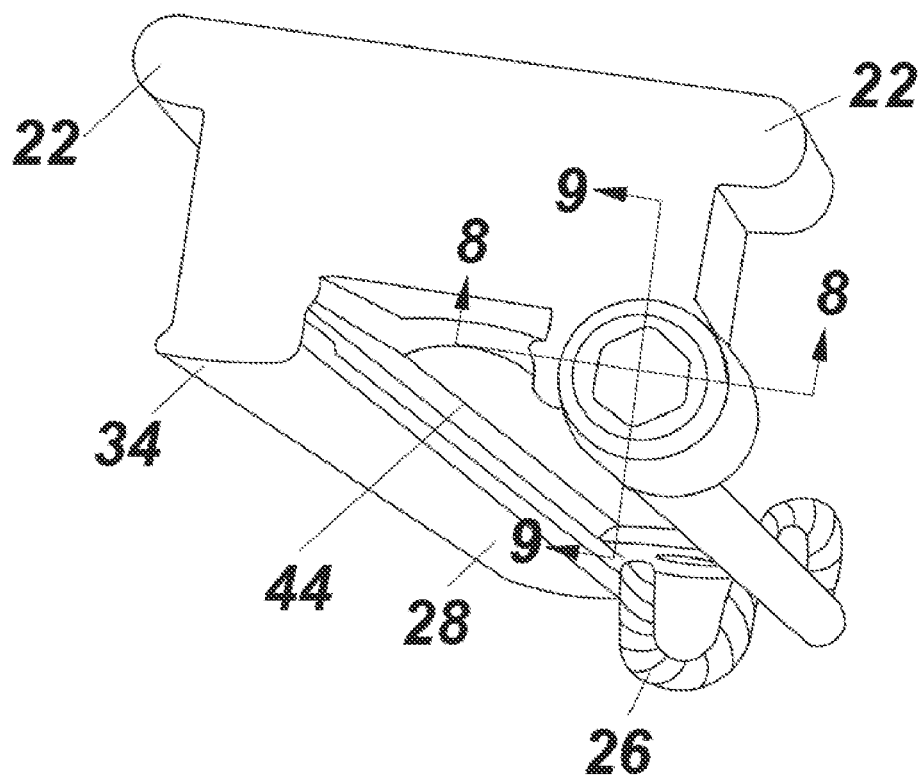
FIG. 5 is a top front right perspective view of the retractor distractor blade.
Figure 6:
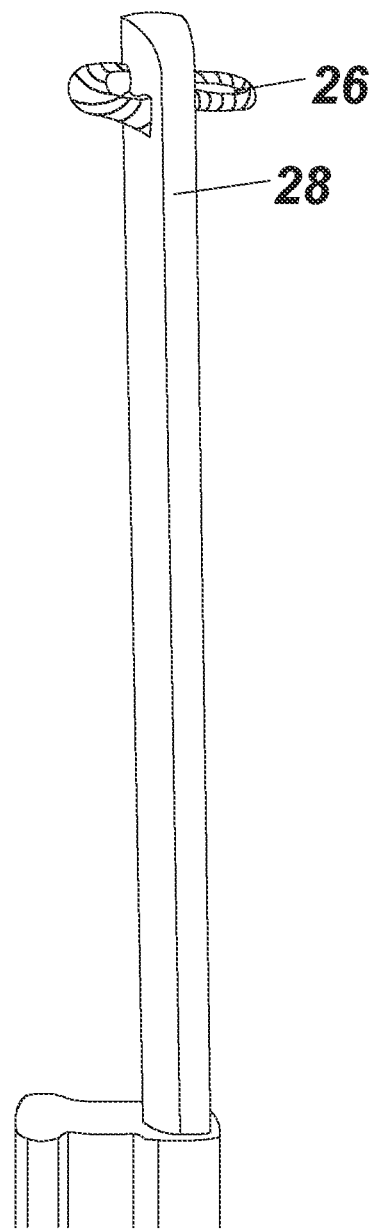
FIG. 6 is a right side view of the retractor distractor blade.
Figure 7:
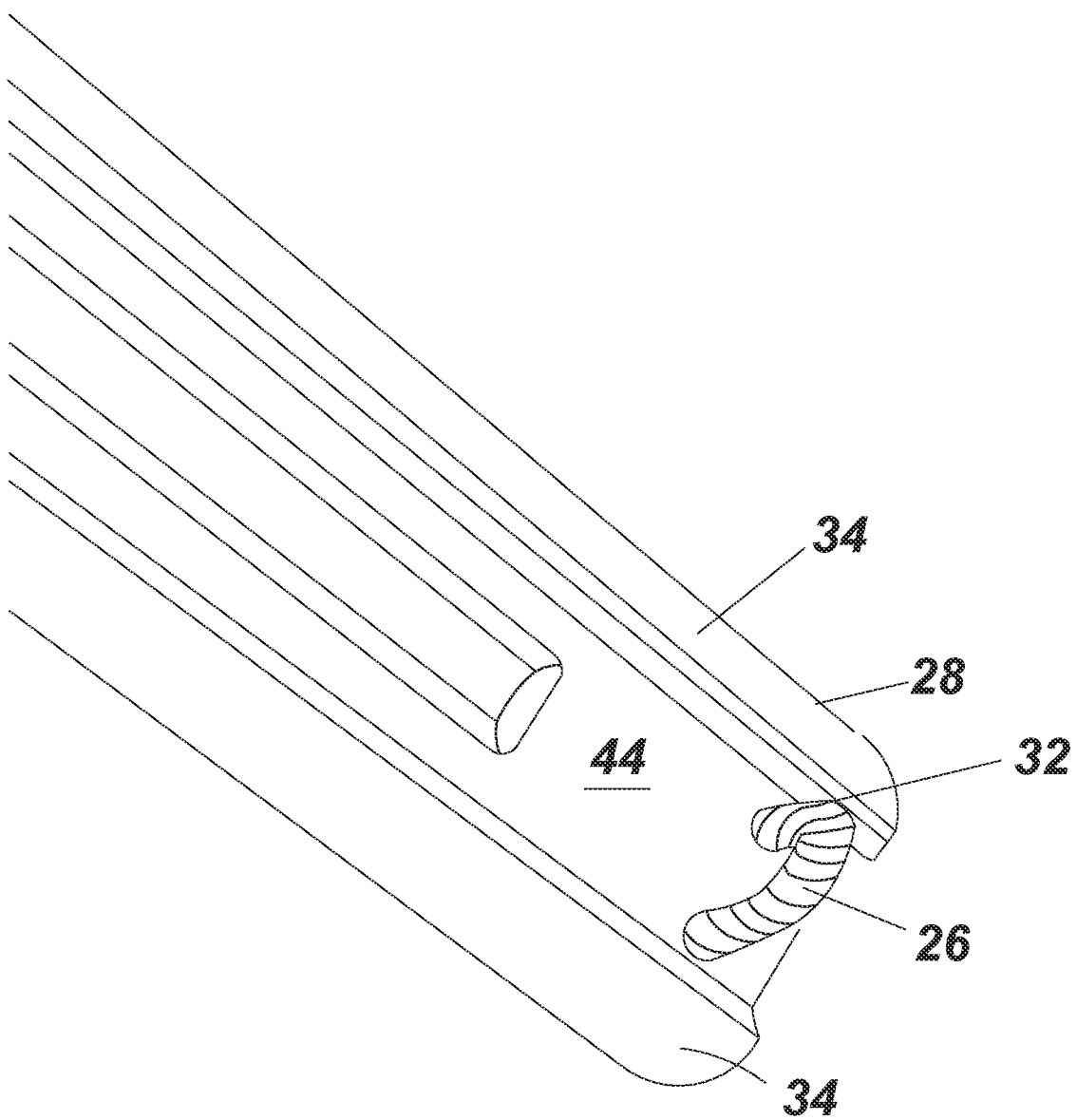
FIG. 7 is a partial front view illustrating the flexible lasso.
Figure 8:
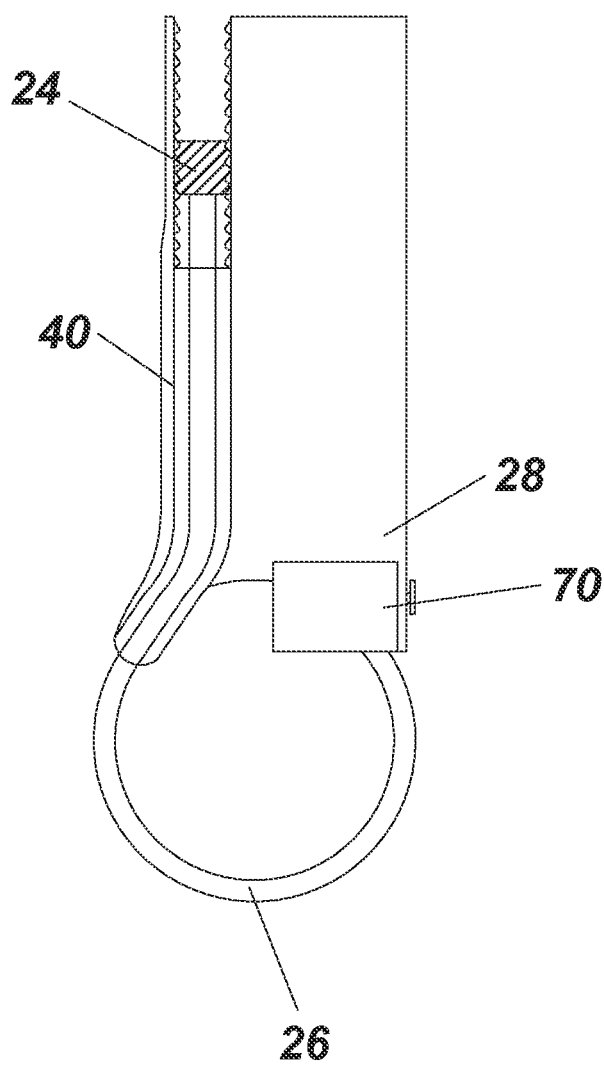
FIG. 8 is a section view taken along lines 8-8 of FIG. 5, illustrating the flexible lasso and the connection to the threaded member.
Figure 9:
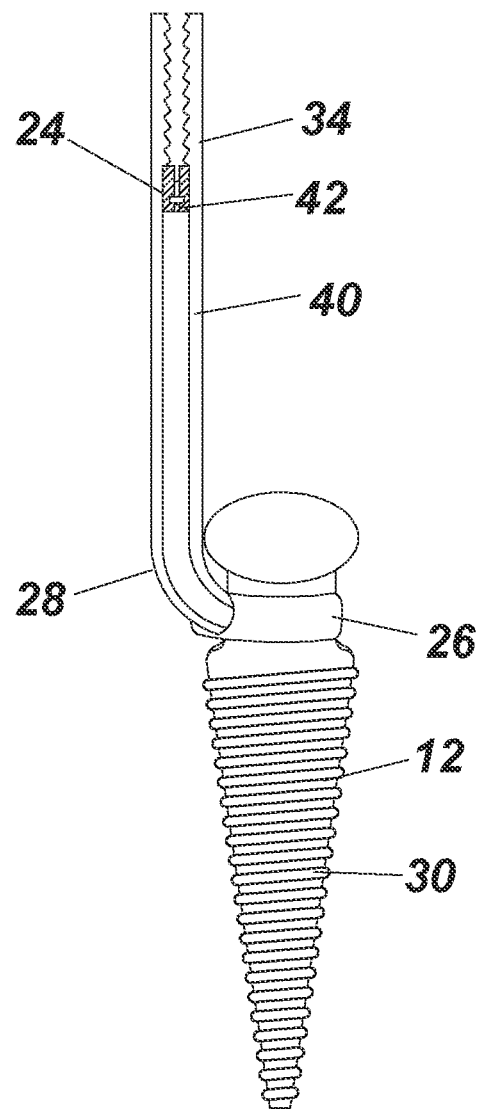
FIG. 9 is a section view taken along lines 9-9 of FIG. 5, illustrating the lasso member connection to the pedicle screw.
Figure 10:
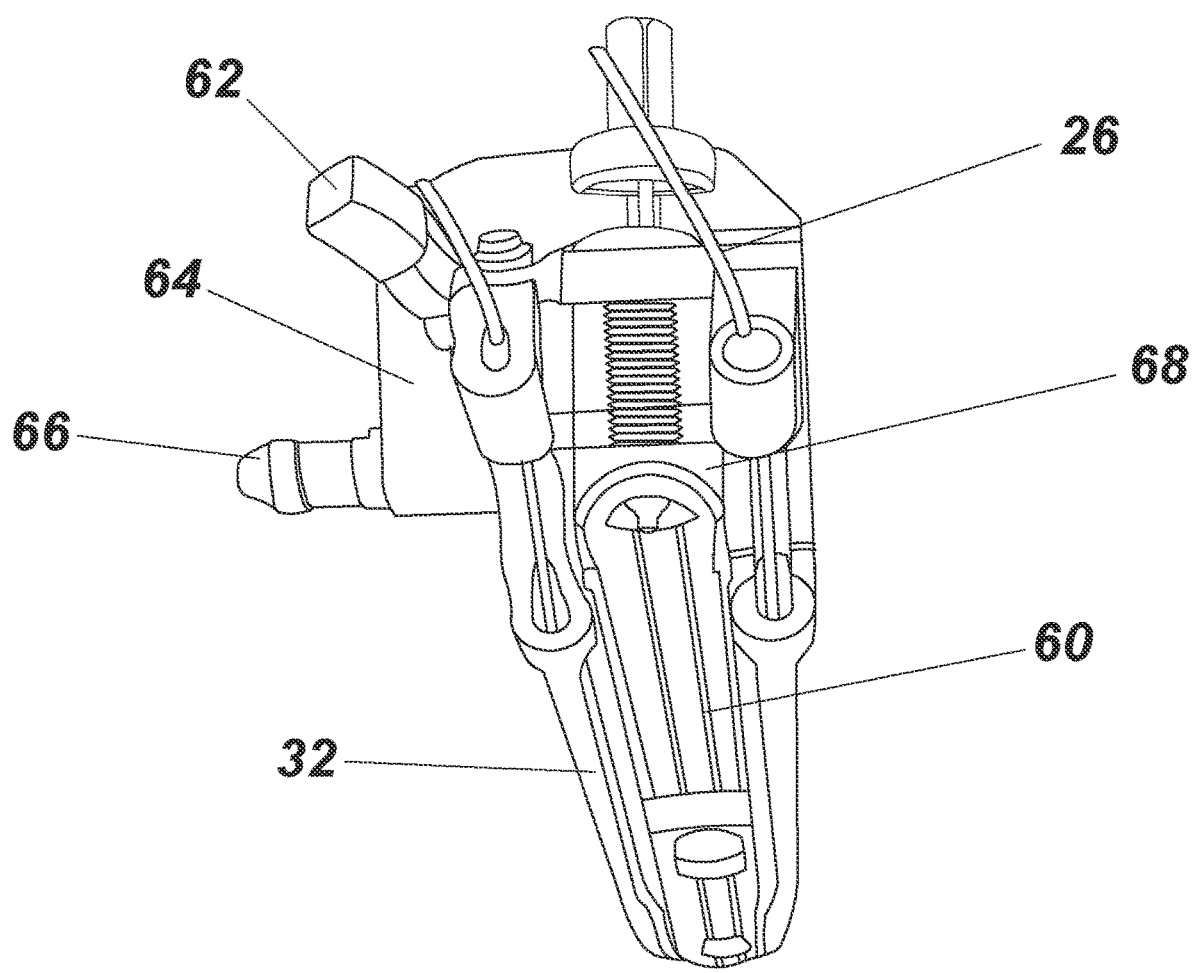
FIG. 10 is a partial top perspective view illustrating a tilting embodiment of the retractor distractor blade.
Figure 11:
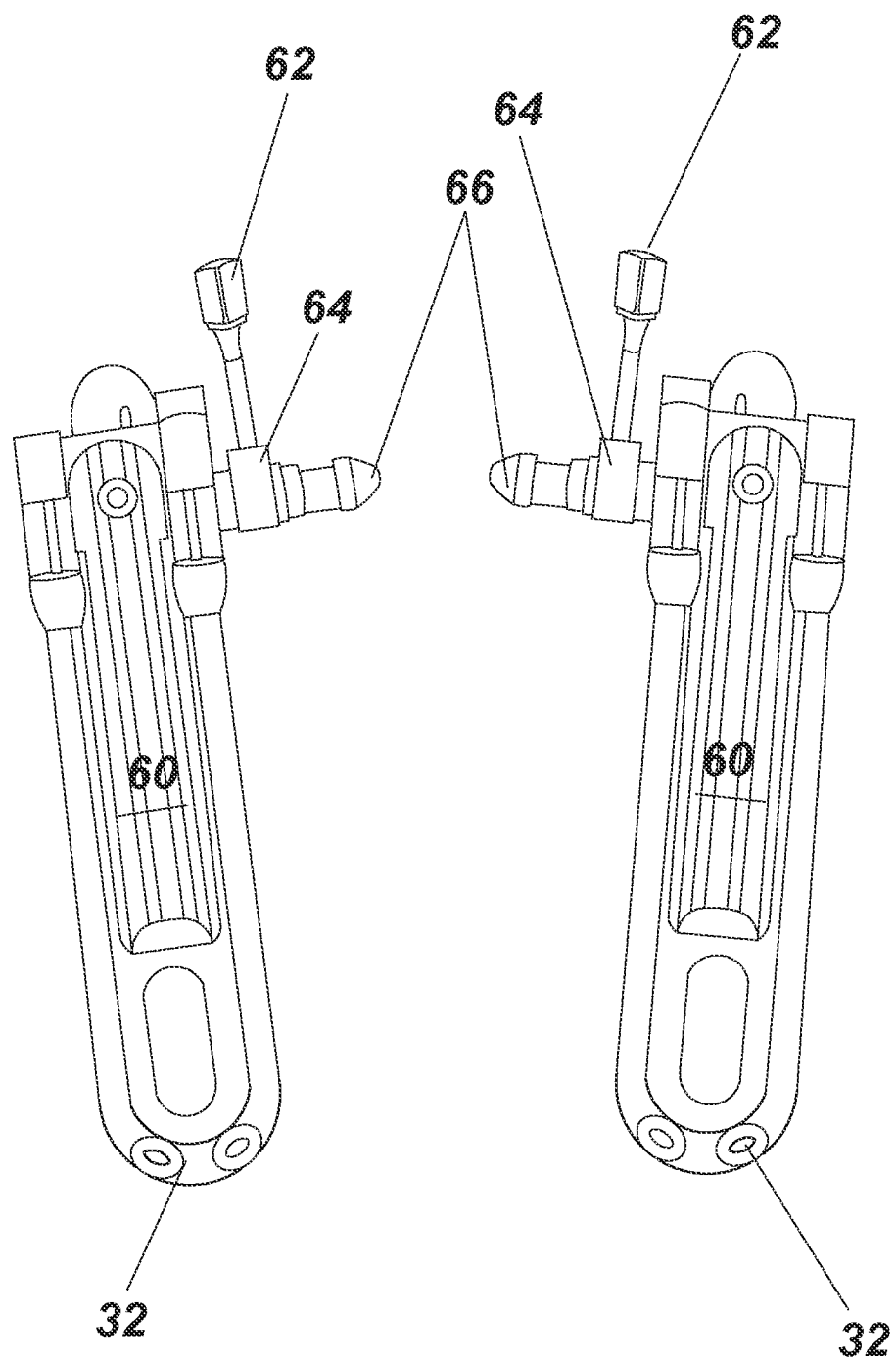
FIG. 11 is a side perspective view illustrating a pair of retractor distractor blades.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Referring generally to FIGS. 1-12, a blade system 100 for use with a retractor or distractor that allows the retractor or distractor to provide a visual pathway to the surgical site, as well as providing distraction to vertebrae without removing the distractor from the surgical site, is illustrated. The retraction distraction blade system 100 is suitable for use with new or pre-existing retractor and distractor tools 10 for the implantation of intervertebral implants 12 into the spine 14 area of an animal, particularly a human. The first end 16 of each retractor distractor blade 18 includes structures for attaching the blade 18 to a retractor or distractor tool 10. The attachment structures may include, but should not be limited to, fastener apertures 20, keys in the form of shaped structures 22 and the like. In at least one embodiment, illustrated in FIGS. 10-12, the attachment structure includes an outrigger assembly (64) which may be fastened to or integrally formed as a portion of the retractor blade 18. In at least one embodiment, the outrigger assembly is secured to a rear surface (68) of the retractor blade. The outrigger assembly may include a post member 66 that is constructed and arranged to cooperate with an arm of the retractor distractor (10) for attachment thereto. This construction provides rotation of the retractor blade (18) with respect to the retractor distractor (10) for angling the retractor blade (18) with respect to the arm of the retractor distractor. A jack bolt (62) is provided in the outrigger (64), which allows the user to adjust and fix the angle between the retractor blade (18) and the retractor distractor (10). The first end 16 of the retractor blade (18) also preferably includes a threaded member 24 connected to a flexible lasso 26 that extends to the second end 28 for securement around a portion of an implant 12, particularly in the form of a pedicle or bone screw 30. A swivel 42 (FIG. 9) is preferably utilized as a connection between the threaded member 24 and the lasso 26. In this manner, the threaded member 24 can be easily rotated without rotation of the lasso 26. The lasso 26 is preferably a flexible member, such as a metal cable, provided with a suitable covering to reduce marring of the pedicle screw 30. However, woven or braided fibers, such as Kevlar carbon fiber or the like, may be substituted for the metal cable without departing from the scope of the invention. It should also be noted that a plurality of interlocking links (not shown) may be utilized in place of the cable or fibers so long as the links, when connected, are suitably flexible to be secured around a portion of the pedicle screw. Coatings, sheaths or the like may be utilized to cushion the outer surface of the links to prevent marring of the screw.

The second end 28 of the retractor distractor blade 18 may also include a guide 32 constructed and arranged for directing the flexible lasso 26 into a loop for attachment around the pedicle screw 30. The guide 32 may be formed as a tubular member extending outwardly from the inner surface 44 of the blade 18 to support the lasso 26 in a position suitable for capturing the pedicle screw 30 into the lasso 26. AN anchor point or member (70) positioned to anchor the distal end of the lasso (26). In this manner, the lasso 26 may be flaccid when formed from cable, fibers, or links, or it may be semi rigid, sufficient to hold itself substantially perpendicular with respect to the blade 18, without departing from the scope of the invention. Once the lasso 26 is secured around the pedicle screw 30, the threaded member 24 at the first end 16 of the blade 18 can be utilized to tighten the lasso 26 to the pedicle screw 30. Once secured, the retractor is prevented from undesirably moving out of the surgical site. This allows the surgeon to work unimpeded to prepare the disc space while the access channel is maintained. Operation of the distractor or retractor tool 10 can then be utilized to provide distraction to the spinal vertebrae for implant insertion or spinal alignment while simultaneously providing the retraction needed to perform the surgery. The lassos 26 secure the pedicle screws 30 to the blade 18, and thus the retractor distractor blade system 100 to allow the surgeon to provide distraction, via the retraction or distraction tool 10, while the surgeon can see clearly into the surgical site. Once the procedure is sufficiently complete, the lasso 26 is loosened with the threaded member 24, and the lassos 26 can be removed from the pedicle screws 30. It should be noted that the blades may still be used to maintain access to the surgical area for the duration of the procedure, even after the lassos are uncoupled from the screws.

The blade 18 is preferably constructed from a sufficiently rigid material to withstand the loads caused from providing access to the surgical site which includes the displacement of tissue, as well as the force required to provide distraction of the vertebrae. Therefore, the blade 18 should be constructed from a material such as metal, and more preferably stainless steel, titanium, fiber reinforced polymers or suitable combinations thereof. The blade 18 may also include strengthening ribs 34, or the like, extending the length or a portion of the length of the blade 18. One or more of the strengthening ribs 34 may be hollow or tubular 40 to allow the lasso 26 to extend therethrough. In this manner, the lasso 26 is covered and protected for the length of the blade 18, and the blade 18 is strengthened against bending during use. In a most preferred embodiment, the outer perimeter surface 36 includes a cylindrical radius along the length of the blade 18 to reduce the occurrence of the edges 38 causing damage to the surrounding tissue of the patient during use. The edges 38 are also preferably rounded to reduce damage to tissue during use.

Figure 12:
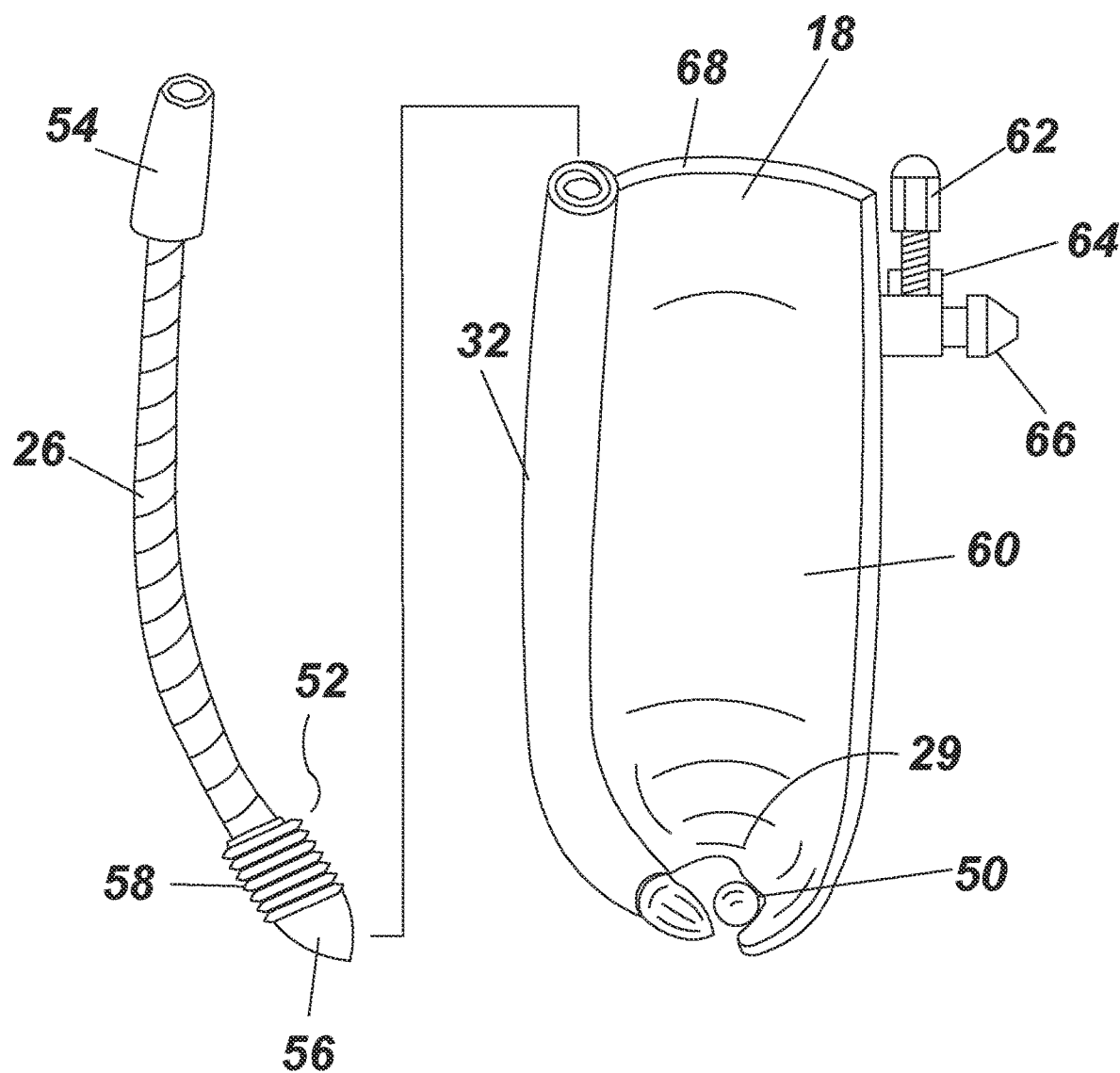
FIG. 12 illustrates an embodiment wherein the cable is used in compression to position the screw against a portion of the retractor distractor blade.

Referring generally to FIGS. 1-12, and more particularly to FIG. 12, an embodiment utilizing the lasso 26 in compression, instead of tension, is illustrated. In this embodiment, the cable, e.g. lasso 26, includes a driving member 54 secured to a first end of the cable and a bullet portion 52 secured to the cable at a second end. The bullet portion 52 includes a tapered, or more preferably a roundly tapered (ogive shaped) portion 56, and a threaded portion 58. This construction allows the lasso 26 to be threaded into position within the tubular guide 32, which extends along the elongate body portion 60 of the retractor blade 18 and includes matching threads. In this manner, the lasso is guided and prevented from buckling when placed in a compressive load. However, it should be noted that by threading a portion of the bullet end, the lasso receives very little compressive load and provides rotary forces to cause rotation of the bullet portion 52. In another embodiment, the driving member 54 is threaded and the bullet portion simply slides into the guide 32; in this embodiment, the tubular guide 32 may provide side support to the cable member (lasso 26). The tubular guide 32 is preferably curved or angled along the side of the retractor blade 18 to direct the tapered portion 56 of the bullet portion 52 toward an opposite side of the retractor blade to create a grasping assembly 29. The grasping assembly 29 may be provided with a seat 50, which is preferably V-shaped and positioned so that when a shaft of a bone screw is positioned in the seat 50, a side or end surface of the tapered portion creates a three point contact to the screw shaft. It should be noted that when the side surface of the tapered or roundly tapered portion contacts the screw shaft, a mechanical advantage is provided to multiply the forces applied to the lasso 26 to cause its rotation. The mechanical advantage can be varied by changing the radius or angle of the side surface where it contacts the screw 30. Release of the screw 30 is accomplished by simply rotating the driving member 54 in an opposite direction with respect to that of tightening the grasping assembly 29 to cause the bullet portion 52 to retract into the tubular guide 32. The retractor blade 18 may be provided with various structures for attaching the blade to a retractor or distractor, or a combination retractor distractor, without departing from the scope of the invention, including bolts, pins, clamps, posts 62 and the like. In at least one embodiment, the retractor blade 18 is provided with the outrigger assembly 64 and a jack bolt 62 for establishing the desired angle between the retractor distractor tool and the retractor blade.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention, which are obvious to those skilled in the art, are intended to be within the scope of the following claims.

What is claimed is:

1. A blade system (100) for a surgical retractor tool (10), the surgical retractor tool (10) having a body including a plurality of arms moveable away from each other or towards each other in a controlled manner, comprising:

a retractor blade (18) for attachment to one of the plurality of arms of the surgical retractor tool (10), the retractor blade (18) having an elongate body portion (60), the elongate body portion (60) configured to extend from a position outside of an animal body to a spine bone of the animal body, the retractor blade (18) being configured to contact and distract tissue surrounding the retractor blade (18) to provide a visual pathway to a surgical site, a first end (16) of the retractor blade (18) including structures for attaching the retractor blade (18) to the retractor tool (10), a second end (28) of the retractor blade (18) including a grasping assembly (29) for grasping a bone screw (30), the grasping assembly (29) including a flexible lasso (26) having a length extending from the first end (16) to the second end (28) of the retractor blade (18), and configured to be attached around a portion of the bone screw (30) to thereby secure the second end (28) of the retractor blade (18) to the bone screw (30), the bone screw (30) securable to a bone for securing the retractor blade (18), and thus the surgical retractor tool (10), in position with respect to the bone screw.

2. The blade system (100) for a surgical retractor tool (10) as claimed in claim 1, wherein, when the bone screw (30) is secured to bone, the surgical retractor tool (10) may be operated by movement of one or more of the plurality of arms whereby the connection between the retractor blade (18) and the bone screw (30) enables distraction of bones in addition to the retraction of tissue.

3. The blade system (100) for a surgical retractor tool (10) as claimed in claim 1, the flexible lasso (26) includes a loop at the second end (28) of the retractor blade (18) for securement around a portion of the bone screw (30).

4. The blade system (100) for a surgical retractor tool (10) as claimed in claim 3, wherein the flexible lasso (26) is metal cable.

5. The blade system (100) for a surgical retractor tool (10) as claimed in claim 3, wherein the retractor blade (18) includes a guide (32) extending along a length of the retractor blade (18) for guiding the flexible lasso (26).

6. The blade system (100) for a surgical retractor tool (10) as claimed in claim 5, wherein the guide (32) is a tubular member.

7. The blade system (100) for a surgical retractor tool (10) as claimed in claim 5, wherein the second end (28) of the retractor blade (18) includes a seat (50) for locating the pedicle screw (30) with respect to the second end (28) of the retractor blade (18).

8. The blade system (100) for a surgical retractor tool (10) as claimed in claim 7, wherein the flexible lasso (26) includes a bullet end (52) and a cable is used in compression to force the bullet end (52) into a side surface of the pedicle screw (30) to secure the retractor blade (18) to the pedicle screw (30).

9. The blade system (100) for a surgical retractor tool (10) as claimed in claim 8, wherein the guide (32) is constructed and arranged to prevent the flexible lasso (26) from buckling under compressive loads.

10. The blade system (100) for a surgical retractor tool (10) as claimed in claim 7, wherein the lasso (26) includes a bullet portion (52) on a second end thereof and a driving member (54) on an opposite first end, the bullet portion (52) including a tapered portion (56) and a threaded side surface (58), the guide (32) including matching threads so that the flexible lasso (26) can be used for rotation of the bullet end (52) to provide a compression force to a side surface of the pedicle screw (30) to secure the retractor blade (18) to the pedicle screw (30).

11. The blade system (100) for a surgical retractor tool (10) as claimed in claim 10, wherein the tapered portion (56) is roundly tapered.

12. The blade system (100) for a surgical retractor tool (10) as claimed in claim 10, wherein the seat (50) is V-shaped.

13. The blade system (100) for a surgical retractor tool (10) as claimed in claim 10, wherein the seat (50) and the tapered portion (56) provide a three point contact to the pedicle screw (30).

14. The blade system (100) for a surgical retractor tool (10) as claimed in claim 5, wherein the retractor blade (18) includes an anchor point (70) for securing a distal end of the flexible lasso (26).

15. The blade system (100) for a surgical retractor tool (10) as claimed in claim 1, wherein the flexible lasso (26) includes a threaded member (24) connected to the flexible lasso (26), the threaded member (24) positioned on the first end (16) of the retractor blade (18) for controlling the length of the flexible lasso (26).

16. The blade system (100) for a surgical retractor tool (10) as claimed in claim 4, wherein the threaded member (24) is connected to the flexible lasso (26) with a swivel (42) so that the threaded member (24) can be easily rotated without rotation of the lasso (26).

17. A blade system (100) for a surgical retractor tool (10), the surgical retractor tool (10) having a body including a plurality of arms moveable away from each other or towards each other in a controlled manner, comprising:

a retractor blade (18) for attachment to one of the plurality of arms of the surgical retractor tool (10), the retractor blade (18) having an elongate body portion (60), the elongate body portion (60) configured to extend from a position outside of an animal body to a spine bone of the animal body, the retractor blade (18) being configured to contact and distract tissue surrounding the retractor blade (18) to provide a visual pathway to a surgical site, a first end (16) of the retractor blade (18) including structures for attaching the retractor blade (18) to the retractor tool (10), a second end (28) of the retractor blade (18) including a grasping assembly (29) for grasping a bone screw (30), the bone screw (30) securable to a bone for securing the retractor blade (18), and thus the surgical retractor tool (10), in position with respect to the bone screw, wherein the retractor blade (18) includes an outrigger assembly (64) for attachment to one of the plurality of arms of the retractor distractor (10), the outrigger assembly (64) secured to a rear surface (68) of the retractor blade (18), and wherein the outrigger assembly (64) includes a post member (66) positioned to engage an aperture of the retractor tool (10) for rotational movement around a central axis of the post member (66), and wherein the outrigger assembly (64) includes a jack bolt (62), the jack bolt (62) positioned to cooperate with a portion of the retractor tool (10) to provide angular adjustment and fixation to the rotation between the retractor blade (18) and the retractor tool (10).

18. A blade system (100) for a surgical retractor tool (10), the surgical retractor tool (10) having a body including a plurality of arms moveable away from each other or towards each other in a controlled manner, comprising:

a retractor blade (18) for attachment to one of the plurality of arms of the surgical retractor tool (10), the retractor blade (18) having an elongate body portion (60), the elongate body portion (60) configured to extend from a position outside of an animal body to a spine bone of the animal body, the retractor blade (18) being configured to contact and distract tissue surrounding the retractor blade (18) to provide a visual pathway to a surgical site, a first end (16) including structures for attaching the retractor blade (18) to the retractor tool (10), a second end (28) including a grasping assembly (29) for grasping a bone screw (30), the grasping assembly (29) including a flexible lasso (26) having a length extending from the first end (16) and configured to form a loop at the second end (28) of the retractor blade (18), the loop configured to be attached around a portion of the bone screw (30) and to be adjusted between a loose and a tightened configuration to thereby releasably secure the second end (28) of the retractor blade (18) to the bone screw (30), the bone screw (30) securable to a bone for securing the retractor blade (18), and thus the surgical retractor tool (10), in position with respect to the bone screw.

19. The blade system (100) for a surgical retractor tool (10) as claimed in claim 18, the grasping assembly (29) including a threaded member (24) connected to the flexible lasso (26) and positioned at the first end (16) of the retractor blade (18) for controlling the length of the flexible lasso (26) to thereby tighten or loosen securement of the flexible lasso to the portion of the bone screw.

* * * * *